(12) United States Patent
Ito et al.

(10) Patent No.: US 9,593,170 B2
(45) Date of Patent: Mar. 14, 2017

(54) COMPOUND, PHOTOCURABLE COMPOSITION, AND METHODS FOR PRODUCING PATTERNED FILM, OPTICAL COMPONENT, CIRCUIT BOARD, ELECTRONIC COMPONENT BY USING THE PHOTOCURABLE COMPOSITION, AND CURED PRODUCT

(71) Applicant: CANON KABUSHIKI KAISHA, Tokyo (JP)

(72) Inventors: Toshiki Ito, Kawasaki (JP); Takeshi Honma, Tokyo (JP); Shiori Yonezawa, Tokyo (JP); Hitoshi Sato, Utsunomiya (JP); Youji Kawasaki, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/889,793

(22) PCT Filed: May 2, 2014

(86) PCT No.: PCT/JP2014/002399
§ 371 (c)(1),
(2) Date: Nov. 6, 2015

(87) PCT Pub. No.: WO2014/181533
PCT Pub. Date: Nov. 13, 2014

(65) Prior Publication Data
US 2016/0108142 A1 Apr. 21, 2016

(30) Foreign Application Priority Data
May 9, 2013 (JP) .................. 2013-099551

(51) Int. Cl.
| | | |
|---|---|---|
| *C08F 2/50* | (2006.01) | |
| *C08F 2/46* | (2006.01) | |
| *C08G 61/04* | (2006.01) | |
| *C07C 217/08* | (2006.01) | |
| *G03F 7/00* | (2006.01) | |
| *H01L 21/02* | (2006.01) | |
| *H01L 21/308* | (2006.01) | |
| *H01L 21/311* | (2006.01) | |
| *C07C 217/40* | (2006.01) | |
| *G02B 1/12* | (2006.01) | |
| *H05K 3/00* | (2006.01) | |
| *H05K 3/30* | (2006.01) | |

(52) U.S. Cl.
CPC .............. *C08F 2/50* (2013.01); *C07C 217/08* (2013.01); *C07C 217/40* (2013.01); *G02B 1/12* (2013.01); *G03F 7/0002* (2013.01); *H01L 21/02118* (2013.01); *H01L 21/3081* (2013.01); *H01L 21/311* (2013.01); *H05K 3/0076* (2013.01); *H05K 3/0079* (2013.01); *H05K 3/0082* (2013.01); *H05K 3/30* (2013.01); *H05K 2203/0548* (2013.01)

(58) Field of Classification Search
CPC ........... C08F 2/50; G02B 1/12; H05K 3/0079; H05K 3/30; H05K 2203/0548; H05K 3/0076; H05K 3/0082; C07C 217/40; C07C 217/08; G03F 7/0002; H01L 21/3081; H01L 21/02118; H01L 21/311
USPC .............. 522/28, 7, 6, 1, 71, 189, 184; 520/1
See application file for complete search history.

(56) References Cited

U.S. PATENT DOCUMENTS

| | | |
|---|---|---|
| 3,997,609 A | 12/1976 | Martini et al. |
| 2003/0072713 A1 | 4/2003 | Platzek et al. |

(Continued)

FOREIGN PATENT DOCUMENTS

| | | |
|---|---|---|
| CN | 87106226 A | 3/1988 |
| CN | 1259933 A | 7/2000 |

(Continued)

OTHER PUBLICATIONS

Szabo et al, Jul. 4, 2006, Novel generation ponytails in fluorous chemistry: Syntheses of primary, secondary, and tertiary (nanafluoro-tert-butyloxy)ethyl amines, Journal of Fluorine Chemistry 127, 1496-1504.*

(Continued)

*Primary Examiner* — Ling Choi
*Assistant Examiner* — Jessica E Whiteley
(74) *Attorney, Agent, or Firm* — Canon USA, Inc. IP Division

(57) ABSTRACT

A compound that increases the photocuring rate of a photocurable composition and reduces the force for releasing a cured product from a mold is provided.

A compound is represented by general formula (1):
where $R_f$ represents an alkyl group at least part of which is substituted with fluorine, $R_O$ represents an oxyalkylene group or a repeated structure of an oxyalkylene group, N represents a nitrogen atom, $R_A$ represents an alkyl group, and $R_B$ represents an alkyl group or a hydrogen atom.

[Chem. 1]

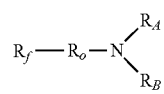

General formula (1)

23 Claims, 2 Drawing Sheets

(56) References Cited

U.S. PATENT DOCUMENTS

2006/0094882 A1* 5/2006 Umemoto ............ C07C 211/63
                                                        546/347
2007/0020183 A1  1/2007 Schirmer et al.

FOREIGN PATENT DOCUMENTS

| | | | |
|---|---|---|---|
| CN | 1461750 | A | 12/2003 |
| CN | 1666149 | A | 9/2005 |
| JP | 02-172944 | A | 7/1990 |
| JP | 2007084625 | A | 4/2007 |
| JP | 2010-114209 | * | 5/2010 |
| JP | 2010114209 | A | 5/2010 |
| JP | 2012-033517 | * | 2/2012 |
| JP | 2012033517 | A | 2/2012 |
| JP | 2013253150 | A | 12/2013 |
| JP | 2014078697 | A | 5/2014 |
| JP | 2014082469 | A | 5/2014 |
| WO | 2013069511 | A1 | 5/2013 |

OTHER PUBLICATIONS

Fujita, JP 2010-114209 Part 1 Machine Translation, May 20, 2010.*
Fujita, JP 2010-114209 Part 2 Machine Translation, May 20, 2010.*
Yonezawa, JP 2012-033517 Machine Translation, Feb. 16, 2012.*
V.E. Pashinnik, "Amino-trifluorosulfuranes with Electron-acceptor Fluoroalkyl and Heterocyclic Groups at the Nitrogen Atom", Ukranian Chemical Journal, 2007, pp. 45-50, vol. 73, No. 1.
Catalog Name (CO) : Aurora Building Blocks; Chemcat (STN) [online]; 2014.
Denes Szabo, et al.; "Novel Generation Ponytails in Fluorous Chemistry: Syntheses of Primary, Secondary, and Tertiary (nonafluoro-tert-butyloxy)ethylamines"; Journal of Fluorine Chemistry, V127, 2006, p. 1496-1504.
STN Database Registry—CAS: 1495958-05-8(STN: Dec. 16, 2013),1467207-10-8(STN: Nov. 1, 2013),1247198-71-5(STN:Oct. 26, 2010),1282491-59-1(STN: Apr. 19, 2011), 1249236-34-7(STN: Oct. 31, 2010), 1251110-55-0(STN: Nov. 2, 2010),1249371-68-3(STN: Oct. 31, 2010),1472689-94-3(STN: Nov. 13, 2013),1494332-53-4(STN:Dec. 13, 2013).

* cited by examiner

COMPOUND, PHOTOCURABLE COMPOSITION, AND METHODS FOR PRODUCING PATTERNED FILM, OPTICAL COMPONENT, CIRCUIT BOARD, ELECTRONIC COMPONENT BY USING THE PHOTOCURABLE COMPOSITION, AND CURED PRODUCT

TECHNICAL FIELD

The present invention relates to a compound, a photocurable composition, and methods for producing a patterned film, an optical component, a cured product, a circuit board, and an electronic component by using the photocurable composition.

BACKGROUND ART

A photo-(nano)imprint method is one of the techniques for producing patterned resist films on substrates such as processing substrates.

A photo-(nano)imprint method that includes a long irradiation step has a disadvantage of low productivity. If force (mold releasing force) required to separate a mold from a cured resist is large, various problems such as defects in the pattern and degradation of alignment accuracy resulting from detachment of a substrate from a stage can occur.

To overcome these disadvantages, Japanese Patent Laid-Open No. 2010-114209 discloses a photo-(nano)imprint method in which a hydrogen donor is added to a photocurable composition to improve the photocuring rate.

Japanese Patent Laid-Open No. 2007-084625 discloses a technique of adding a fluorine-based surfactant to a photocurable composition to decrease the mold releasing force. However, a further improvement on photocuring rate is needed to improve the productivity and a technique that can further decrease the mold releasing force from the mold is in demand.

CITATION LIST

Patent Literature

PTL 1: Japanese Patent Laid-Open No. 2010-114209
PTL 2: Japanese Patent Laid-Open No. 2007-084625

SUMMARY OF INVENTION

The present invention provides a compound represented by general formula (1).

[Chem. 1]

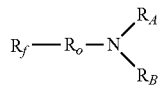

General Formula (1)

In general formula (1), $R_f$ represents an alkyl group at least part of which is substituted with fluorine, $R_O$ represents an oxyalkylene group or a repeated structure of an oxyalkylene group, N represents a nitrogen atom, $R_A$ represents an alkyl group, and $R_B$ represents an alkyl group or a hydrogen atom.

The present invention can provide a photocurable composition having high sensitivity capable of forming a cured product that can be released from a mold with less force, a compound that realizes such properties, and methods for producing a film, an optical component, a circuit board, and an electronic component by using the photocurable composition.

DESCRIPTION OF EMBODIMENTS

Figure 1A:
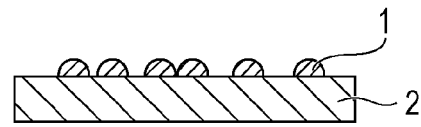
FIG. 1A is a schematic cross-sectional view showing an example of a method for producing a film according to one embodiment.

Embodiments of the present invention will now be described in detail with reference to drawings. These embodiments do not limit the scope of the present invention. The embodiments described below are subject to alterations, modifications, improvements, etc., based on the common knowledge of persons skilled in the art within the scope of the gist of the present invention and such alterations etc., are within the scope of the present invention.

A photocurable composition according to one embodiment contains a component (A), a component (B), and a component (C):

(A) a polymerizable compound
(B) a photopolymerization initiator
(C) a hydrogen donor represented by general formula (1) below.

[Chem. 2]

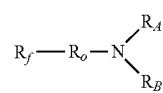

General formula (1)

In general formula (1), $R_f$ represents an alkyl group at least part of which is substituted with fluorine, $R_O$ represents an oxyalkylene group or a repeated structure of an oxyalkylene group, N represents a nitrogen atom, $R_A$ represents an alkyl group, and $R_B$ represents an alkyl group or a hydrogen atom.

Detailed descriptions of these components are as follows.
Component (A): Polymerizable Compound
The component (A) is a polymerizable compound. In this embodiment and the present invention, a polymerizable compound is a compound that reacts with a polymerizing factor (such as a radical) generated from a photopolymerization initiator (component (B) described below) and forms a film of a polymer compound as a result of chain reaction (polymerization reaction).

Examples of the polymerizable compound include radical polymerizable compounds. The polymerizable compound used as the component (A) may be constituted by one polymerizable compound or two or more polymerizable compounds.

The radical polymerizable compound may be a compound having one or more acryloyl groups or methacryloyl groups.

Examples of a monofunctional (meth)acryl compound having one acryloyl group or a methacryloyl group include, but are not limited to, phenoxyethyl(meth)acrylate, phenoxy-2-methyl ethyl(meth)acrylate, phenoxy ethoxy ethyl (meth)acrylate, 3-phenoxy-2-hydroxy propyl(meth)acrylate, 2-phenyl phenoxy ethyl(meth)acrylate, 4-phenyl phenoxy ethyl(meth)acrylate, 3-(2-phenylphenyl)-2-hydroxypropyl (meth)acrylate, EO-modified p-cumylphenol(meth)acrylate, 2-bromophenoxyethyl(meth)acrylate, 2,4-dibromophenoxyethyl(meth)acrylate, 2,4,6-tribromophenoxyethyl(meth) acrylate, EO-modified phenoxy(meth)acrylate, PO-modified phenoxy(meth)acrylate, polyoxyethylene nonylphenyl ether (meth)acrylate, isobornyl(meth)acrylate, 1-adamantyl(meth) acrylate, 2-methyl-2-adamantyl(meth)acrylate, 2-ethyl-2-adamantyl(meth)acrylate, bornyl(meth)acrylate, tricyclodecanyl(meth)acrylate, dicyclopentanyl(meth)acrylate, dicyclopentenyl(meth)acrylate, cyclohexyl(meth)acrylate, 4-butylcyclohexyl(meth)acrylate, acryloyl morpholine, 2-hydroxyethyl(meth)acrylate, 2-hydroxypropyl(meth)acrylate, 2-hydroxybutyl(meth)acrylate, methyl(meth)acrylate, ethyl(meth)acrylate, propyl(meth)acrylate, isopropyl(meth) acrylate, butyl(meth)acrylate, amyl(meth)acrylate, isobutyl (meth)acrylate, t-butyl(meth)acrylate, pentyl(meth)acrylate, isoamyl(meth)acrylate, hexyl(meth)acrylate, heptyl(meth) acrylate, octyl(meth)acrylate, isooctyl(meth)acrylate, 2-ethylhexyl(meth)acrylate, nonyl(meth)acrylate, decyl(meth) acrylate, isodecyl(meth)acrylate, undecyl(meth)acrylate, dodecyl(meth)acrylate, lauryl(meth)acrylate, stearyl(meth) acrylate, isostearyl(meth)acrylate, benzyl(meth)acrylate, tetrahydrofurfuryl(meth)acrylate, butoxyethyl(meth)acrylate, ethoxy diethylene glycol(meth)acrylate, polyethylene glycol mono(meth)acrylate, polypropylene glycol mono(meth) acrylate, methoxyethylene glycol(meth)acrylate, ethoxyethyl(meth)acrylate, methoxy polyethylene glycol(meth)acrylate, methoxy polypropylene glycol(meth)acrylate, diacetone(meth)acrylamide, isobutoxymethyl(meth)acrylamide, N,N-dimethyl(meth)acrylamide, t-octyl(meth)acrylamide, dimethylaminoethyl(meth)acrylate, diethylaminoethyl(meth)acrylate, 7-amino-3,7-dimethyloctyl(meth) acrylate, N,N-diethyl(meth)acrylamide, and N,N-dimethylaminopropyl(meth)acrylamide.

Examples of the commercially available products of the monofunctional (meth)acryl compounds include, but are not limited to, ARONIX M101, M102, M110, M111, M113, M117, M5700, TO-1317, M120, M150, and M156 (products of Toagosei Co., Ltd.), MEDOL 10, MIBDOL 10, CHDOL 10, MMDOL 30, MEDOL 30, MIBDOL 30, CHDOL 30, LA, IBXA, 2-MTA, HPA, and Viscoat #150, #155, #158, #190, #192, #193, #220, #2000, #2100, and #2150 (products of Osaka Organic Chemical Industry Ltd.), LIGHT ACRYLATE BO-A, EC-A, DMP-A, THF-A, HOP-A, HOA-MPE, HOA-MPL, PO-A, P-200A, NP-4EA, and NP-8EA, and EPOXY ESTER M-600A (products of Kyoeisha Chemical Co., Ltd.), KAYARAD TC110S, R-564, and R-128H (products of NIPPON KAYAKU Co. Ltd.), NK ESTER AMP-10G and AMP-20G (products of Shin-Nakamura Chemical Co., Ltd.), FA-511A, 512A, and 513A (products of Hitachi Chemical Co., Ltd.), PHE, CEA, PHE-2, PHE-4, BR-31, BR31M, and BR-32 (products of Dai-Ichi Kogyo Seiyaku Co., Ltd.), VP (product of BASF), and ACMO, DMAA, and DMAPAA (products of KOHJIN Holdings Co., Ltd.).

Examples of the polyfunctional (meth)acryl compounds having two or more acryloyl groups or methacryloyl groups include, but are not limited to, trimethylolpropane di(meth) acrylate, trimethylolpropane tri(meth)acrylate, EO-modified trimethylolpropane tri(meth)acrylate, PO-modified trimethylolpropane tri(meth)acrylate, EO-, PO-modified trimethylolpropane tri(meth)acrylate, pentaerythritol tri(meth)acrylate, pentaerythritol tetra(meth)acrylate, ethylene glycol di(meth)acrylate, tetraethylene glycol di(meth)acrylate, polyethylene glycol di(meth)acrylate, polypropylene glycol di(meth)acrylate, 1,4-butanediol di(meth)acrylate, 1,6-hexanediol di(meth)acrylate, neopentyl glycol di(meth)acrylate, tris(2-hydroxyethyl) isocyanurate tri(meth)acrylate, tris (acryloyloxy) isocyanurate, bis(hydroxymethyl) tricyclodecane di(meth)acrylate, dipentaerythritol penta (meth)acrylate, dipentaerythritol hexa(meth)acrylate, EO-modified 2,2-bis(4-((meth)acryloxy)phenyl)propane, PO-modified 2,2-bis(4-((meth)acryloxy)phenyl)propane, and EO-, PO-modified 2,2-bis(4-((meth)acryloxy)phenyl) propane.

Examples of the commercially available products of the polyfunctional (meth)acryl compounds include YUPIMER UV SA1002 and SA2007 (products of Mitsubishi Chemical Corporation), Viscoat #195, #230, #215, #260, #335HP, #295, #300, #360, #700, GPT, and 3PA (products of Osaka Organic Chemical Industry Ltd.), LIGHT ACRYLATE 4EG-A, 9EG-A, NP-A, DCP-A, BP-4EA, BP-4PA, TMP-A, PE-3A, PE4A, and DPE-6A (products of Kyoeisha Chemical Co., Ltd.), KAYARAD PET-30, TMPTA, R-604, DPHA, DPCA-20, -30, -60, -120, HX-620, D-310, and D-330 (products of NIPPON KAYAKU Co. Ltd.), ARONIX M208, M210, M215, M220, M240, M305, M309, M310, M315, M325, and M400 (products of Toagosei Co., Ltd.), and Ripoxy VR-77, VR-60, and VR-90 (products of Showa Highpolymer Co., Ltd.).

In the compound groups described above, "(meth)acrylate" refers to an acrylate and an equivalent methacrylate having an alcohol residue. A "(meth)acryloyl group" refers to an acryloyl group and an equivalent methacryloyl group having an alcohol residue. EO represents ethylene oxide. An EO-modified compound A refers to a compound in which a (meth)acrylic acid residue of a compound A is bonded to an alcohol residue of the compound A via a block structure of an ethylene oxide group. PO represents propylene oxide. A PO-modified compound B refers to a compound in which a (meth)acrylic acid residue of a compound B is bonded to an alcohol residue of the compound B via a block structure of a propylene oxide group.

Component (B): Photopolymerization Initiator

The component (B) is a photopolymerization initiator.

In this embodiment and the present invention, a photopolymerization initiator is a compound that generates a polymerizing factor (radical) upon sensing light of a particular wavelength. In particular, a photopolymerization initiator generates a radical (radical generator) when irradiated with light (radiations such as infrared rays, visible rays, ultraviolet rays, far ultraviolet rays, X-rays, and charged particle beams such as electron beams). To be more specific, the photopolymerization initiator is a photopolymerization initiator that generates a radical when irradiated with light having a wavelength in the range of 190 to 700 nm, for example.

The photopolymerization initiator serving as the component (B) may be constituted by one photopolymerization initiator or two or more photopolymerization initiators.

Examples of the radical generator include substituted or unsubstituted 2,4,5-triaryl imidazole dimers such as a 2-(o-chlorophenyl)-4,5-diphenylimidazole dimer, a 2-(o-chlorophenyl)-4,5-di(methoxyphenyl)imidazole dimer, a 2-(o-fluorophenyl)-4,5-diphenylimidazole dimer, and a 2-(o- or p-methoxyphenyl)-4,5-diphenylimidazole dimer; benzophenone derivatives such as benzophenone, N,N'-tetramethyl-4,4'-diaminobenzophenone (Michler's ketone), N,N'-tetraethyl-4,4'-diaminobenzophenone, 4-methoxy-4'-dimethylaminobenzophenone, 4-chlorobenzophenone, 4,4'-dimethoxybenzophenone, and 4,4'-diaminobenzophenone; aromatic ketone derivatives such as 2-benzyl-2-dimethylamino-1-(4-morpholinophenyl)-butanone-1,2-methyl-1-[4-(methyl thio)phenyl]-2-morpholino-propanone-1-on; quinones such as 2-ethylanthraquinone, phenanthrenequinone, 2-t-butylanthraquinone, octamethylanthraquinone, 1,2-benzanthraquinone, 2,3-benzanthraquinone, 2-phenylanthraquinone, 2,3-diphenylanthraquinone, 1-chloroanthraquinone, 2-methylanthraquinone, 1,4-naphthoquinone, 9,10-phenanthraquinone, 2-methyl-1,4-naphthoquinone, and 2,3-dimethylanthraquinone; benzoin ether derivatives such as benzoin methyl ether, benzoin ethyl ether, and benzoin phenyl ether; benzoin derivatives such as benzoin, methyl benzoin, ethyl benzoin, and propyl benzoin; benzyl derivatives such as benzyl dimethyl ketal; acridine derivatives such as 9-phenyl acridine and 1,7-bis(9,9'-acridinyl)heptane; N-phenyl glycine derivatives such as N-phenyl glycine; acetophenone derivatives such as acetophenone, 3-methyl acetophenone, acetophenone benzyl ketal, 1-hydroxycyclohexyl phenyl ketone, and 2,2-dimethoxy-2-phenyl acetophenone; thioxanthone derivatives such as thioxanthone, diethylthioxanthone, 2-isopropylthioxanthone, and 2-chlorothioxanthone; and xanthone, fluorenone, benzaldehyde, fluorene, anthraquinone, triphenylamine, carbazole, 1-(4-isopropylphenyl)-2-hydroxy-2-methylpropan-1-on, 2-hydroxy-2-methyl-1-phenylpropan-1-on, 2,4,6-trimethylbenzoyl diphenylphosphine oxide, and bis-(2,6-dimethoxybenzoyl)-2,4,4-trimethylpentylphosphine oxide.

Examples of commercially available products of the radical generators include, but are not limited to, Irgacure 184, 369, 651, 500, 819, 907, 784, and 2959, CGI-1700, -1750, and -1850, CG24-61, Darocur 1116 and 1173, Lucirin TPO, LR8893, and LR8970 (products of BASF), and EBECRYL P36 (product of UCB).

The blend ratio of the photopolymerization initiator serving as the component (B) in the photocurable composition is 0.01% by weight or more and 10% by weight or less and preferably 0.1% by weight or more and 7% by weight or less relative to the total weight of the polymerizable compound serving as the component (A).

When the blend ratio of the photopolymerization initiator relative to the total weight of the polymerizable compound is 0.01% by weight or more, a satisfactory curing rate is achieved. At a blend ratio of 10% by weight or less, a cured product obtained from the photocurable composition can exhibit good mechanical properties.

Component (C): Hydrogen Donor

The component (C) is a hydrogen donor.

In this embodiment and the present invention, a hydrogen donor is a compound that reacts with an initiation radical generated from the photopolymerization initiator serving as the component (B) or a radial at a polymerization propagating terminal so as to give a radical having a higher reactivity and accelerate the polymerization of the component (A).

The function of the component (C) as the hydrogen donor can be confirmed by comparing the polymerization rate of a photocurable composition between when the component (C) is used and when not used and confirming that a photocurable composition containing the component (C) exhibits a higher polymerization rate.

The hydrogen donor serving as the component (C) is a compound represented by general formula (1) below.

[Chem. 3]

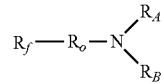

General formula (1)

In general formula (1), $R_f$ represents an alkyl group at least part of which is substituted with fluorine, $R_O$ represents an oxyalkylene group or a repeated structure of an oxyalkylene group, N represents a nitrogen atom, $R_A$ represents an alkyl group, and $R_B$ represents an alkyl group or a hydrogen atom.

$R_f$ in general formula (1) represents an alkyl group at least part of which is substituted with fluorine. $R_f$ may be an alkyl group having all of hydrogen atoms substituted with fluorine or an alkyl group having some of hydrogen atoms substituted with fluorine.

An example of an alkyl group having some of hydrogen atoms substituted with fluorine is a group represented by general formula (2) below.

[Chem. 4]

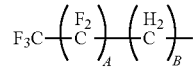

General formula (2)

In general formula (2), A represents an integer of 1 or more and 25 or less and B represents an integer of 1 or more and 25 or less.

For $R_O$ representing an oxyalkylene group or a repeated structure of an oxyalkylene group in general formula (1), examples of the oxyalkylene group include an oxyethylene group and an oxypropylene group and examples of the repeated structure of an oxyalkylene group include a repeated structure of the oxyethylene group and a repeated structure of the oxypropylene group. Specific examples of the oxyethylene group or the repeated structure of the oxyethylene group include divalent groups represented by general formula (3) below and specific examples of the oxypropylene group or the repeated structure of the oxypropylene group include divalent groups represented by general formula (4) below:

—(OCH$_2$CH$_2$)$_a$—      General formula (3)

(where a represents an integer of 1 or more and 100 or less)

—(OCH$_2$CH(CH$_3$))$_b$—      General formula (4)

(where b represents an integer of 1 or more and 100 or less)

A hydrogen donor represented by general formula (1) has a secondary or tertiary amino group functioning as a hydrogen donating group and thus accelerates the polymerization of the component (A) which is a polymerizable compound. The hydrogen donor presumably also functions as a surfactant since it has the $R_f$ group (alkyl group at least part of which is substituted with fluorine) serving as an oleophobic segment and the $R_O$ group (oxyalkylene group or repeated structure of oxyalkylene group) serving as an oleophilic segment. Due to this, the component (C) behaves like common surfactants, and segregates at the interface between a mold and the photocurable composition and forms a very thin releasing layer between the mold and the photocurable composition in a placement step (1) or a mold contact step (2) in a method for producing a patterned film by using the photopolymerizable composition of the embodiment described below. This releasing layer is non-polymerizable and the molecules in the layer are not covalently bonded with one another. Thus, separation occurs at the interface between the releasing layer and the photocurable composition layer or inside the releasing layer, and a cured film formed by polymerization of the photocurable composition can be easily released from the mold.

Since the hydrogen donor represented by general formula (1) has a secondary or tertiary amino group, hydroxyl groups of the quartz which is commonly used as a material for molds and the secondary or tertiary amino group forms ionic bonds. This is presumably why the cured product can be released from a mold with a relatively low mold releasing force at a lamellar interface of the releasing layer in a mold releasing step (4) in a method for producing a patterned film by using the photopolymerizable composition of the embodiment described below.

The alkyl group represented by $R_A$ in general formula (1) may be linear or cyclic but is preferably linear and more preferably a linear alkyl group having 1 to 5 carbon atoms. $R_B$ in general formula (1) may represent a hydrogen atom or an alkyl group but preferably represents an alkyl group which may be linear or cyclic as in $R_A$. $R_B$ preferably represents a linear alkyl group and more preferably a linear alkyl group having 1 to 5 carbon atoms. Examples of the linear alkyl group having 1 to 5 carbon atoms in $R_A$ and $R_B$ include a methyl group, an ethyl group, a propyl group, a butyl group, and a pentyl group.

$R_B$ preferably represents an alkyl group because the effect of accelerating polymerization of the component (A), which is a polymerizable compound, is higher when the hydrogen donor represented by general formula (1) has a tertiary amino group.

Specific examples of the hydrogen donor represented by general formula (1) include compounds represented by general formula (5) below.

[Chem. 5]

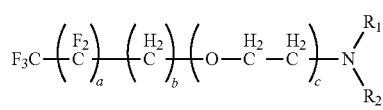

General formula (5)

In general formula (5), a represents an integer within the range of 1 to 25, b represents an integer within the range of 0 to 25, c represents an integer within the range of 1 to 25, $R_1$ represents an alkyl group, and $R_2$ represents an alkyl group or hydrogen.

In general formula (5), a represents an integer within the range of 1 to 25 and preferably an integer within the range of 1 to 10. Also, b represents an integer within the range of 0 to 25, preferably an integer within the range of 1 to 25, and more preferably an integer within the range of 1 to 5. In general formula (5), c represents an integer within the range of 1 to 25 and preferably an integer within the range of 1 to 10. When a, b, and c each independently represent an integer within the range of 1 to 10, a compound represented by general formula (5) can be easily synthesized. This is so particularly when b represents an integer within the range of 1 to 5.

In general formula (5), $R_2$ preferably represents an alkyl group (in other words, the compound represented by general formula (5) is preferably a tertiary amino group) and more preferably a linear alkyl group having 1 to 5 carbon atoms. This is because, as discussed above, the effect of accelerating polymerization of the component (A) is enhanced when $R_1$ and $R_2$ each represent an alkyl group, in particular, a linear alkyl group having 1 to 5 carbon atoms.

For example, $R_1$ and $R_2$ may each represent a linear alkyl group or a cyclic alkyl group. Examples of the linear alkyl group having 1 to 5 carbon atoms include a methyl group, an ethyl group, a propyl group, a butyl group, and a pentyl group.

Specific examples of the compound represented by general formula (5) include compounds represented by general formula (6) below and compounds represented by general formula (7) below.

[Chem. 6]

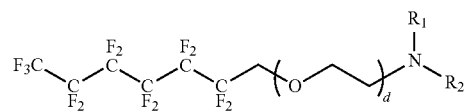

General formula (6)

In general formula (6), d represents an integer in the range of 1 to 10 and $R_1$ and $R_2$ each represent an alkyl group.

[Chem. 7]

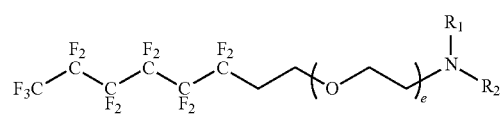

General formula (7)

In general formula (7), e represents an integer in the range of 1 to 10 and $R_1$ and $R_2$ each represent an alkyl group.

A specific example of the compound represented by general formula (6) is a compound represented by formula (A) below and a specific example of the compound represented by general formula (7) is a compound represented by formula (B) below.

[Chem. 8]

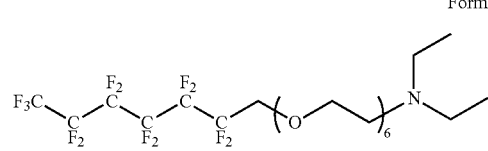

Formula (A)

-continued

[Chem. 9]

Formula (B)

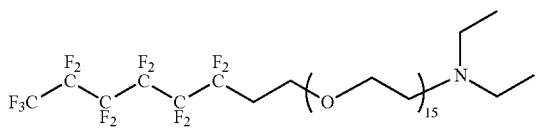

The hydrogen donor represented by general formula (1) may be a compound represented by general formula (8) below.

[Chem. 10]

General formula (8)

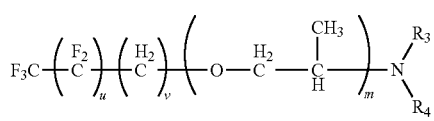

In general formula (8), u represents an integer in the range of 1 to 25, v represents an integer in the range of 0 to 25, m represents an integer in the range of 1 to 25, $R_3$ represents an alkyl group, and $R_4$ represents an alkyl group or hydrogen.

In general formula (8), u, v, and m preferably each independently represent an integer in the range of 1 to 10 and more preferably an integer in the range of 1 to 5.

This is because it becomes easier to synthesize a compound represented general formula (8) when u, v, and m each independently represent an integer in the range of 1 to 10 and in particular when v represents an integer in the range of 1 to 5.

In general formula (8), $R_3$ and $R_4$ preferably each represent an alkyl group and more preferably an alkyl group having 1 to 5 carbon atoms.

For example, $R_3$ and $R_4$ may each represent a linear alkyl group or a cyclic alkyl group. Examples of the alkyl group having 1 to 5 carbon atoms include a methyl group, an ethyl group, a propyl group, a butyl group, and a pentyl group.

The compound represented by general formula (1) can be synthesized by the following synthetic schemes, for example. Compounds represented by general formulae (5), (6), (7), (8), (9), and (10), and formulae (A) and (B), can also be synthesized in the same manner

[Chem. 11]

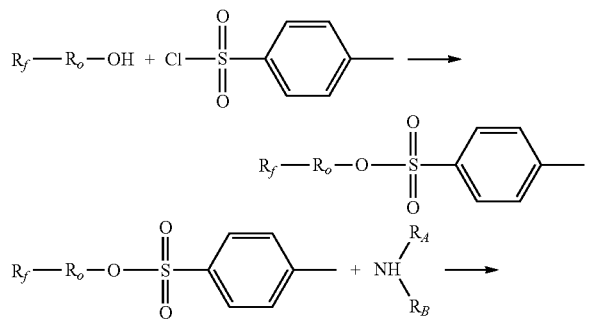

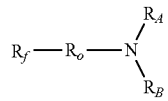

The compound (C) represented by general formula (1) may be constituted by two or more hydrogen donors represented by general formula (1). Compounds represented by general formula (9) below are naturally one of the compounds represented by general formula (1):

$Rf_1$-Rc-X  General formula (9)

where $Rf_1$ represents a group constituted by fluorine and carbon atoms only or a group constituted by fluorine, carbon, and hydrogen atoms only, Rc represents a group constituted by at least one selected from a polyethylene oxide group, a polypropylene oxide group, and an alkylene group, and X represents an amino group.

Specific examples of the polyoxyalkylene group in general formula (9) include a polyethylene oxide group and a polyoxypropylene group. Specific examples of the polyethylene oxide group include divalent groups represented by general formula (3) above and specific examples of the polypropylene oxide group include divalent groups represented by general formula (4) above.

In general formula (9), X may be a primary, secondary, or tertiary amino group but is preferably a secondary or tertiary amino group. This is because a secondary amino group and a tertiary amino group have a higher polymerization accelerating effect than a primary amino group.

Examples of the hydrogen donor represented by general formula (9) include compounds represented by general formula (10) below.

[Chem. 12]

General formula (10)

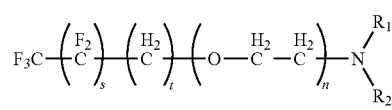

In general formula (10), s represents an integer in the range of 1 to 25, t and n each independently represent an integer in the range of 0 to 25 where at least one of t and n represents an integer of 1 or more, $R_1$ represents an alkyl group, and $R_2$ represents an alkyl group or hydrogen.

The blend ratio of the hydrogen donor serving as the component (C) in the photocurable composition according to this embodiment may be 0.001% by weight or more and 10% by weight or less relative to the total weight of the polymerizable compound serving as the component (A). The blend ratio of the hydrogen donor is preferably 0.002% by weight or more and 5% by weight or less and more preferably 0.005% by weight or more and 3% by weight or less relative to the total weight of the polymerizable compound serving as the component (A). If the blend ratio is less than 0.001% by weight, a sufficient polymerization accelerating effect may not be exhibited. At a blend ratio exceeding 10% by weight, the mechanical strength of a photocured product obtained after curing may be insufficient.

Other Additives

The photocurable composition of this embodiment may contain additives in addition to the component (A), the component (B), and the component (C) described above depending on the purpose as long as the effect of the invention is not impaired. Examples of the additives include a releasing agent, a surfactant, a sensitizer, an antioxidant, a solvent, and a polymer component.

A sensitizer accelerates the initiation reaction of photoradical polymerization through exchange of energy or electrons and is a compound added to accelerate polymerization reaction and improve reaction conversion rate. An example of the sensitizer is a sensitizing dye.

A sensitizing dye is a compound that is excited by absorption of light of a particular wavelength and interacts with a polymerization initiator serving as the component (B). The interaction refers to, for example, migration of energy or migration of electrons from a sensitizing dye in an excited state to a photopolymerization initiator serving as the component (B).

Specific examples of the sensitizing dye include, but are not limited to, anthracene derivatives, anthraquinone derivatives, pyrene derivatives, perylene derivatives, carbazole derivatives, benzophenone derivatives, thioxanthone derivatives, xanthone derivatives, coumarin derivatives, phenothiazine derivatives, camphorquinone derivatives, acridine dyes, thiopyrylium salt dyes, merocyanine dyes, quinoline dyes, styrylquinoline dyes, ketocoumarin dyes, thioxanthene dyes, xanthene dyes, oxonol dyes, cyanine dyes, rhodamine dyes, and pyrylium salt dyes.

These sensitizers may be used alone or in combination as a mixture.

The photocurable composition of this embodiment may contain a known hydrogen donor other than the component (C) such as those described in Japanese Patent Laid-Open No. 2010-114209 as an additive.

Specific examples of such a hydrogen donor include, but are not limited to, amine compounds such as N-butylamine, di-n-butylamine, tri-n-butylphosphine, allylthiourea, s-benzylisothiuronium-p-toluene sulfinate, triethylamine, diethylaminoethyl methacrylate, triethylene tetramine, 4,4'-bis(dialkylamino)benzophenone, N,N-dimethylamino benzoic acid ethyl ester, N,N-dimethylamino benzoic acid isoamyl ester, pentyl-4-dimethylaminobenzoate, triethanolamine, and N-phenyl glycine; and mercapto compounds such as 2-mercapto-N-phenyl benzoimidazole and mercaptopropionic acid ester.

In the case where the photocurable composition of this embodiment contains a hydrogen donor other than the component (C) as an additive, this hydrogen donor may be one hydrogen donor or two or more hydrogen donors.

In the case where the photocurable composition of this embodiment contains a sensitizer and/or a hydrogen donor other than the component (C) as the additive, the content thereof is preferably 0% or more and 20% by weight or less, more preferably 0.1% by weight or more and 5.0% by weight or less, and most preferably 0.2% by weight or more and 2.0% by weight or less relative to the total weight of the polymerizable compound serving as the component (A). At a sensitizer content of 0.1% by weight or more, the polymerization accelerating effect can be more effectively exhibited. At a sensitizer content of 5.0% by weight or less, the molecular weight of the polymer compound constituting the photocured product can be sufficiently increased and the dissolution failure and deterioration of storage stability can be suppressed.

The ratios of the component (A), the component (B), and the component (C) can be determined by analyzing a photocured product obtained by curing the photocurable composition of this embodiment through infrared spectrometry, ultraviolet visible light spectroscopy, pyrolysis gas chromatography mass spectroscopy, etc. As a result, the ratios of the component (A), the component (B), and the component (C) in the photocurable composition can be determined.

Temperature at the Time of Blending Photocurable Composition

In preparing the photocurable composition of this embodiment, at least the component (A), the component (B), and the component (C) are mixed and dissolved under particular temperature conditions. To be more specific, mixing and dissolving are performed at a temperature in the range of 0 degrees (Celsius) to 100 degrees (Celsius).

Viscosity of Photocurable Composition

The viscosity of the photocurable composition of this embodiment is preferably 1 cP or more and 100 cP or less, more preferably 5 cP or more and 50 cP or less, and most preferably 6 cP or more and 20 cP or less in terms of the viscosity of a mixture of the components other than the solvent at 23 degrees (Celsius).

When the viscosity of the photocurable composition is 100 cP or less, recesses of a fine pattern on a mold can be filled with the composition in a relatively short time during the process of bringing the photocurable composition in contact with the mold and therefore pattern defects caused by filling failure are decreased. When the viscosity is 1 cP or higher, the photocurable composition can be more evenly applied or, in the process of bringing the photocurable composition into contact with a mold, the photocurable composition may be suppressed from flowing out from an edge of the mold.

Surface Tension of Photocurable Composition

The surface tension of the photocurable composition of this embodiment is preferably 5 mN/m or more and 70 mN/m or less, more preferably 7 mN/m or more and 35 mN/m or less, and most preferably 10 mN/m or more and 32 mN/m or less in terms of the surface tension of a mixture of the components other than the solvent at 23 degrees (Celsius). At a surface tension lower than 5 mN/m, it may take a long time to fill recesses of a fine pattern on a mold with the composition in the process of bringing the photocurable composition into contact with the mold. At a surface tension higher than 70 mN/m, the surface smoothness and flatness may be degraded.

Impurities in Photocurable Composition

The impurity content in the photocurable composition of this embodiment may be as low as possible. Here, the "impurity" refers to those components other than the component (A), the component (B), the component (C), and the additives described above.

The photocurable composition may thus be obtained through a purification step. An example of the purification step is filtration using a filter.

In performing filtration with a filter, for example, the component (A), the component (B), the component (C), and additives used as needed are mixed and then the resulting mixture is filtered through a filter having a pore size of 0.001 micrometers or more and 5.0 micrometers or less. The filtration may be conducted in multiple stages or repeated many times. The filtrate may be filtered again. The filter used for filtration may be, for example, a polyethylene resin filter, a polypropylene resin filter, a fluorine resin filter, or a nylon resin filter but is not limited to these.

Performing such a purification step removes impurities such as particles in the photocurable composition. As a result, it becomes possible to prevent defects in the pattern resulting from undesirable irregularities due to impurities such as particles in the photocured product obtained by curing the photocurable composition.

In the case where the photocurable composition of this embodiment is used for manufacturing semiconductor integrated circuits, entraining of impurities (metal impurities) containing metal atoms into the photocurable composition is to be avoided as much as possible in order not to inhibit the operation of the product. In this case, the metal impurity concentration in the photocurable composition is preferably 10 ppm or less and more preferably 100 ppb or less.

Next, a method for producing a patterned film according to an embodiment is described.

FIGS. 1A to 1F are schematic cross-sectional views showing an example of a method for producing a patterned film according to this embodiment.

The method for producing a patterned film according to this embodiment includes:

(1) a placement step of placing the photocurable composition of the above-described embodiment on a substrate;

(2) a mold contact step of bringing the photocurable composition into contact with a mold;

(3) an irradiation step of irradiating the photocurable composition with light; and (4) a mold releasing step of releasing the cured product obtained in the step (3) from the mold.

The method for producing a patterned film according to this embodiment utilizes a photo-imprinting technique.

A film obtained by the method for producing a patterned film according to this embodiment preferably has a pattern 1 nm to 10 mm in size and more preferably has a pattern 10 nm to 100 micrometers in size. It should be noted here that a pattern forming technique of forming a film having a nano-size (1 nm or more and 100 nm or less) pattern (recesses and protrusions) by using light is called a photo-(nano)imprint method. The method for producing a patterned film according to this embodiment utilizes a photo-(nano)imprint method.

The above-described steps will now be described one by one.

Placement Step (1)

In this step (placement step), as shown in FIG. 1A, a photocurable composition 1 which is the same as the photocurable composition according to the embodiment described above is placed (applied) on a substrate 2 to form a coating film.

The substrate 2 on which the photocurable composition 1 is placed is a processing substrate and is usually a silicon wafer.

The substrate 2 is not limited to a silicon wafer and may be freely selected from substrates for semiconductor devices, such as those composed of aluminum, a titanium-tungsten alloy, an aluminum-silicon alloy, an aluminum-copper-silicon alloy, silicon oxide, and silicon nitride. A substrate that has been subjected to a surface treatment (for example, silane coupling treatment, silazane treatment, organic thin film deposition, or the like) to improve adhesion to the photocurable composition may used as the substrate 2 (processing substrate).

Examples of the method for placing the photocurable composition of this embodiment on the substrate 2 include an ink jet method, a dip coating method, an air knife coating method, a curtain coating method, a wire bar coating method, a gravure coating method, an extrusion coating method, a spin coating method, and a slit scanning method. The thickness of a pattern transfer-receiving layer (coating film) differs depending on the purpose of use but is, for example 0.01 micrometers or more and 100.0 micrometers or less.

Figure 1B:
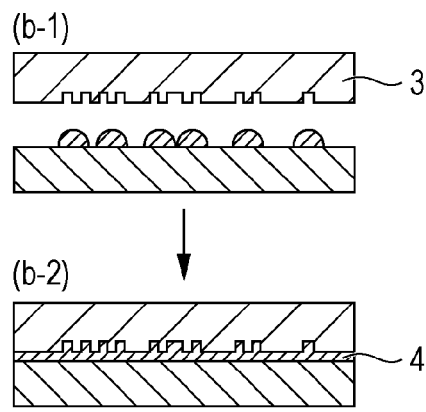
FIG. 1B includes schematic cross-sectional views showing an example of a method for producing a film according to one embodiment.

Mold Contact Step (2) of Bringing Photocurable Composition into Contact with Mold Next, as shown in FIG. 1B, a mold 3 having an original pattern for transferring a pattern shape is brought into contact with the coating film formed of the photocurable composition 1 in the previous step (placement step). As a result of performing this step of bringing the photocurable composition 1 into contact with the mold 3 (FIG. 1B, part (b-1)), recesses in the fine pattern on the surface of the mold 3 are filled with the coating film (or some parts of the coating film) composed of the photocurable composition 1. Thus, a coating film 4 that fills the fine pattern of the mold is formed (FIG. 1B, part (b-2)).

The mold 3 is composed of a light-transmitting material because of the next step (irradiation step). Examples of the material constituting the mold 3 include glass, quartz, light transparent resins such as polymethyl methacrylate (PMMA) and polycarbonate resins, transparent metal vapor-deposited films, flexible films such as polydimethylsiloxane, photocured films, and metal films. In the case where a light transparent resin is used as the material constituting the mold 3, a resin that does not dissolve in the solvent contained in the photocurable composition 1 is preferably selected. The surface of the mold 3 that comes into contact with the photocurable composition is preferably hydrophilic since it becomes easier to form polar bonds between the surface and the Rf groups, the secondary amine groups, and the tertiary amine groups contained in the hydrogen donor serving as the component (C). More preferably, the surface is composed of quartz.

The mold 3 may be surface-treated prior to the step of bringing the photocurable composition in contact with the mold in order to improve the releasing property between the photocurable composition 1 and the surface of the mold 3. An example of the surface treatment method is a method in which a releasing agent is applied to the surface of the mold to form a releasing agent layer. Examples of the releasing agent applied to the surface of the mold include silicon releasing agents, fluorine releasing agents, polyethylene releasing agents, polypropylene releasing agents, paraffin releasing agents, montan releasing agents, and carnauba releasing agents. For example, a commercially available application-type releasing agent such as OPTOOL DSX produced by Daikin Industries Ltd., is suitable for use. These releasing agents may be used alone or in combination. Among these, fluorine releasing agents are particularly preferable.

In this step (mold contact step), as shown in part (b-1) of FIG. 1B, the pressure applied to the photocurable composition 1 in bringing the photocurable composition 1 into contact with the mold 3 is not particularly limited but is usually in the range of 0.1 MPa to 100 MPa, preferably in the range of 0.1 MPa to 50 MPa, more preferably in the range of 0.1 MPa to 30 MPa, and most preferably in the range of 0.1 MPa to 20 MPa.

In this step, the time for which the photocurable composition 1 is contacted with the mold 3 is not particularly limited but is usually in the range of 0.1 sec to 600 sec, preferably in the range of 0.1 sec to 300 sec., more preferably in the range of 0.1 sec to 180 sec, and most preferably in the range of 0.1 sec to 120 sec.

This step may be performed in an air atmosphere, a reduced pressure atmosphere, or an inert gas atmosphere. A reduced pressure atmosphere and an inert gas atmosphere are particularly preferable since adverse effects of oxygen and moisture on photocuring reaction can be avoided. Examples of the inert gas that can be used to perform the step in an inert gas atmosphere include nitrogen, carbon dioxide, helium, argon, various fluorocarbon gases, or any mixture of these. In the case where this step is performed in an atmosphere composed of a particular gas including air, the pressure may be in the range of 0.0001 atm to 10 atm.

The mold contact step may be performed in an atmosphere composed of a gas that contains a condensable gas (hereinafter may be referred to as "condensable gas atmosphere"). In the present invention and specification, a condensable gas refers to a gas that exists as a gas in the atmosphere before the photocurable composition 1 (shape transfer-receiving layer) contacts the mold 3 (FIG. 1B, part (b-1)) in the mold contact step but becomes condensed and liquefies under capillary pressure generated due to the pressure applied as the photocurable composition 1 (shape transfer-receiving layer) contacts the mold 3 and the gas in the atmosphere fills the recesses of the fine pattern on the mold 3 and the space between the mold and the substrate together with the coating film (or some parts of the coating film).

When the mold contact step is performed in an atmosphere composed of a gas containing a condensable gas, the gas filling the recesses of the fine pattern liquefies, bubbles vanish, and thus the photocurable composition can highly fill the fine pattern. The condensable gas may be dissolved in the photocurable composition.

The boiling point of the condensable gas may be any temperature not above the atmosphere temperature of the mold contact step but is preferably in the range of −10 degrees (Celsius) to 23 degrees (Celsius) and more preferably in the range of 10 degrees (Celsius) to 23 degrees (Celsius). In this range, the effect of increasing the filling property brought by the condensable gas is further enhanced.

The vapor pressure of the condensable at an atmosphere temperature of the mold contact step may be any pressure not over the mold pressure applied during the mold contact step and is preferably in the range of 0.1 to 0.4 MPa. In this range, the filling property is further enhanced. At a vapor pressure larger than 0.4 MPa at the atmosphere temperature, the effect of eliminating bubbles may not be always achieved. If the vapor pressure at the atmosphere temperature is less than 0.1 MPa, pressure reduction is necessary and the system tends to be complicated. The atmosphere temperature for the mold contact step may be any but is preferably in the range of 20 degrees (Celsius) to 25 degrees (Celsius).

Examples of the condensable gas include fluorocarbons, e.g., chlorofluorocarbon (CFC) such as trichlorofluoromethane, fluorocarbon (FC), hydrochlorofluorocarbon (HCFC), hydrofluorocarbon (HFC) such as 1,1,1,3,3-pentafluoropropane ($CHF_2CH_2CF_3$, HFC-245fa, or PFP), and hydrofluoroether (HFE) such as pentafluoroethyl methyl ether ($CF_3CF_2OCH_3$ or HFE-245mc).

Among these condensable gases, 1,1,1,3,3-pentafluoropropane (vapor pressure at 23 degrees (Celsius): 0.14 MPa, boiling point: 15 degrees (Celsius)), trichlorofluoromethane (vapor pressure at 23 degrees (Celsius): 0.1056 MPa, boiling point: 24 degrees (Celsius)), and pentafluoroethyl methyl ether are preferable from the viewpoint of high filling property at an atmosphere temperature of 20 degrees (Celsius) or higher and 25 degrees (Celsius) or lower in the mold contact step. From the viewpoint of safety also, 1,1,1,3,3-pentafluoropropane is particularly preferable.

The condensable gases may be used alone or in combination as a mixture. The gas containing a condensable gas may be solely composed of a condensable gas or a gas mixture containing a condensable gas and a non-condensable gas.

Examples of the non-condensable gas include air, nitrogen, carbon dioxide, helium, and argon. From the viewpoint of the filling property, the non-condensable gas to be mixed with a condensable gas may be helium. The non-condensable gas to be mixed with a condensable gas is preferably helium because when the gases in the atmosphere (condensable gas and helium) fill the recess of the fine pattern on the mold 3 in the mold contact step together with the coating film (or some parts of the coating film), the condensable gas liquefies while helium passes through the mold, thereby enhancing the filling property.

Irradiation Step (3) of Irradiating Photocurable Composition with Light

Figure 1C:
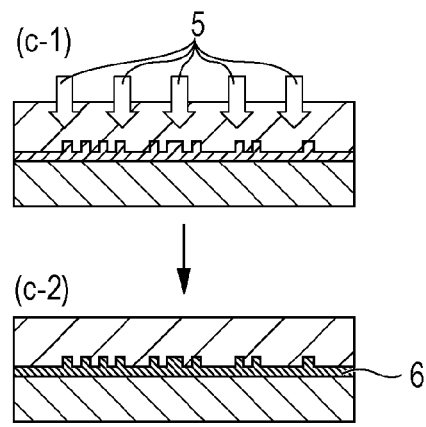
FIG. 1C includes schematic cross-sectional views showing an example of a method for producing a film according to one embodiment.

Next, as shown in FIG. 1C, the portion of the photocurable composition that comes into contact with the mold, in particular, a coating film 4 filling the fine pattern of the mold 3, is irradiated with light through the mold 3 (see part (c-1)). As a result, the coating film 4 filling the fine pattern of the mold and irradiated with light through the mold 3 turns into a cured film 6 (FIG. 1C, part (c-2)).

The light that irradiates the photocurable composition 1 constituting the coating film 4 filling the fine pattern of the mold 3 is selected in accordance with the sensitive wavelength of the photocurable composition 1. In particular, an ultraviolet ray having a wavelength in the range of about 150 nm to about 400 nm, an X-ray, an electron beam, or the like may be used.

Among these, the light (radiation 5) irradiating the photocurable composition 1 is preferably an ultraviolet ray. This is because many of the curing aids (photopolymerization initiators) that are commercially available are sensitive to ultraviolet rays. Examples of the light source of ultraviolet light include a high pressure mercury lamp, an ultra high pressure mercury lamp, a low pressure mercury lamp, a deep-UV lamp, a carbon arc lamp, a chemical lamp, a metal halide lamp, a xenon lamp, a KrF excimer laser, an ArF excimer laser, and a $F_2$ excimer laser. Among these, an ultra high pressure mercury lamp is particularly preferable. The number of the light sources to be used may be one or more. Irradiation may be performed on all or some parts of the coating film 4 filling the fine pattern of the mold.

Irradiation may be performed intermittently two or more times or continuously on all parts. Alternatively, a region A may be irradiated in a first irradiation process and then a region B different from the region A may be irradiated in a second irradiation process.

In this step, the polymerization reaction rate of the photocurable composition under irradiation with light can also be evaluated.

Figure 2:
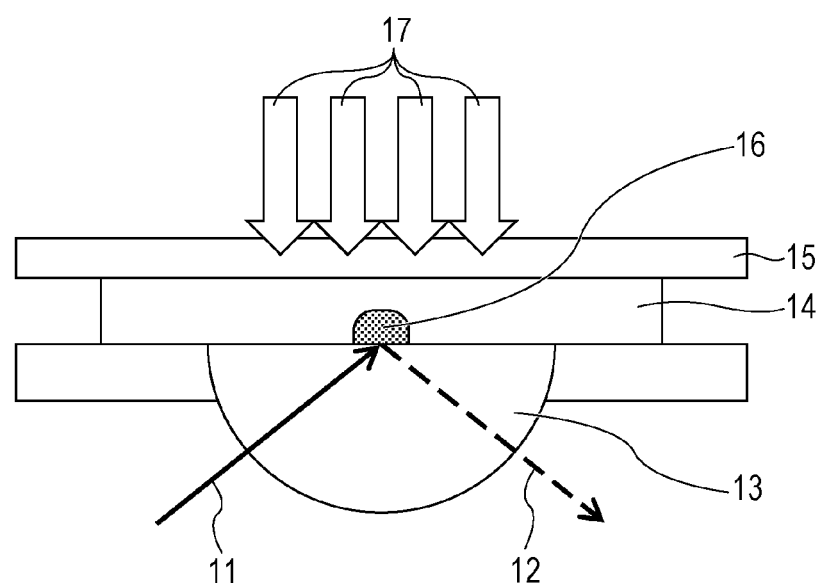
FIG. 2 is a schematic diagram showing an attenuated total reflection infrared spectrometer equipped with an irradiation mechanism.

The polymerization reaction rate of the photocurable composition by irradiation can be measured, for example, with an attenuated total reflection infrared spectrometer equipped with the irradiation mechanism shown in FIG. 2.

Referring to FIG. 2, a photocurable composition 14 is interposed between a diamond ATR crystal 13 of the attenuated total reflection infrared spectrometer and a quartz glass 15. The photocurable composition 14 is cured upon irradiation with light through the quartz glass 15. An infrared ray 11 is applied to the diamond ATR crystal 13 and an evanescent wave 16 that occurs within a several micrometer range above the diamond ATR crystal 13 is detected with a detector 12. Several to several tens of attenuated total reflection infrared spectra of the photocurable composition 14 are acquired per second.

As a result, the infrared spectra of the cured photocurable composition or the photocurable composition in the course of curing can be acquired real-time. The polymerization reaction rate of the photocurable composition can be evaluated by tracking the change in peak intensity attributable to the polymerizable functional group of the component (A) in the acquired infrared spectra.

Mold Releasing Step (4) of Releasing Cured Product from Mold

Next, the cured film 6 is released from the mold 3 so as to form a cured film 7 having a particular pattern shape on the substrate 2.

Figure 1D:
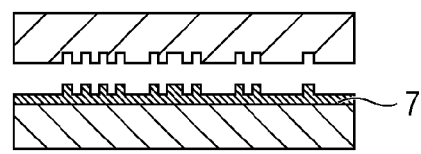
FIG. 1D is a schematic cross-sectional view showing an example of a method for producing a film according to one embodiment.

In this step (mold releasing step), as shown in FIG. 1D, the cured film 6 is released from the mold 3. The reversed pattern of the fine pattern formed on the mold 3 in the step (3) (irradiation step) constitutes the pattern of the patterned cured film 7.

The method for releasing the cured film 6 from the mold 3 may be any method that does not physically destruct part of the cured film 6 during the release. The conditions thereof are also not limited. For example, the substrate 2 (processing substrate) may be fixed and the mold 3 may be moved away from the substrate 2 to perform releasing. Alternatively, the mold 3 may be fixed and the substrate 2 may be moved away from the mold 3 to perform releasing. Both the mold 3 and the substrate 2 may be moved in opposite directions to perform releasing.

When the mold contact step is performed in a condensable gas atmosphere, the condensable gas that has liquefied turns into a gas as the pressure at the interface between the cured film and the mold decreases during the process of releasing the cured film from the mold. As a result, the effect of decreasing the mold releasing force tends to be enhanced.

A cured film having a desirable recess/protrusion pattern shape (the pattern shape derived from the recesses and protrusions on the mold 3) can be obtained through a production process including the steps (1) to (4) described above. The cured film can be used as an optical component, e.g., a Fresnel lens or a diffraction lattice (the film may also be used as a part of an optical component). In such a case, the optical component can include at least the substrate 2 and the patterned cured film 7 on the substrate 2.

Residual Film Removing Step (5) of Removing Part of Cured Film

Figure 1E:
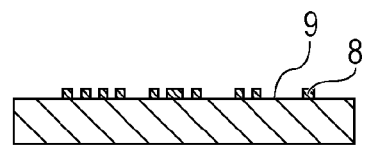
FIG. 1E is a schematic cross-sectional view showing an example of a method for producing a film according to one embodiment.
Figure 1F:
FIG. 1F is a schematic cross-sectional view showing an example of a method for producing a film according to one embodiment.

Although the cured film obtained in the mold releasing step (4) has a particular pattern shape, a part of the film sometimes remains in a region other than where the pattern shape is to be formed (hereinafter, such a part of the film is also referred to as a "residual film"). In such a case, as shown in FIG. 1E, the cured film (residual film) in the regions to be removed is removed from the obtained patterned cured film so as to obtain a cured pattern 8 having a desirable recess/protrusion pattern shape (pattern shape derived from the recesses and protrusions of the mold 3).

An example of the method for removing the residual film is to remove the film (residual film) that forms recesses of the cured film 7 by etching so as to expose the surface of the substrate 2 at the recesses of the pattern of the cured film 7.

The etching method for removing the film at the recesses of the cured film 7 is not particularly limited and a known method, for example, a dry etching method may be employed. A dry etching apparatus known in the art may be used. The source gas for dry etching is appropriately selected in accordance with the element composition of the cured film, which is the film to be etched. Examples of the source gas include halogen gases such as $CF_4$, $C_2F_6$, $C_3F_8$, $CCl_2F_2$, $CCl_4$, $CBrF_3$, $BCl_3$, $PCl_3$, $SF_6$, and $Cl_2$, oxygen-containing gases such as $O_2$, CO, and $CO_2$, inert gases such as He, $N_2$, and Ar, and $H_2$ and $NH_3$. These gases may be used in combination as a mixture.

A cured pattern 8 having a desirable recess/protrusion pattern shape (pattern shape derived from the recesses and protrusions of the mold 3) can be obtained by the production process including the steps (1) to (5) described above. An article having the cured pattern can also be obtained. In the case where the cured pattern 8 is used to process the substrate 2, a substrate processing step (step (6)) below is performed.

The cured pattern 8 may be used as an optical part (or a portion of an optical part) such as a diffraction lattice or a polarizing plate so as to obtain an optical component. In such a case, the optical component may include at least the substrate 2 and the cured pattern 8 on the substrate 2.

Substrate Processing Step (6)

The cured pattern 8 having an recess/protrusion pattern shape obtained by the method for producing a patterned film according to this embodiment can be used as a film for an interlayer insulating film included in an electronic component such as a semiconductor device, e.g., an LSI, a system LSI, a DRAM, a SDRAM, a RDRAM, or a DRDRAM. The cured pattern 8 can also be used as a resist film in the process of producing a semiconductor device.

In the case where the cured pattern 8 is used as a resist film, only the parts of the substrate where the surface is exposed by the etching step (5) (a region 9 in FIG. 1E) are etched or ion-implanted and electronic parts are formed on the substrate. As a result, a circuit board that is constituted by a substrate 2 and a circuit structure 10 (FIG. 1F) based on the pattern shape of the cured pattern 8 and that can be used in semiconductor devices and the like can be obtained. The cured pattern 8 functions as a mask. A controlling mechanism for controlling the circuit board may be provided to the circuit board so as to form an electronic component such as a display, a camera, or medical equipment. Similarly, the cured pattern 8 may be used as a resist film and an optical component may be obtained by performing etching or ion implantation.

Note that in preparing a circuit board or an electronic component, the cured pattern 8 may eventually be removed from the processed substrate. However, a structure that includes the cured pattern 8 as a part of the component is also preferable.

EXAMPLES

The present invention will now be described in further detail by way of Examples which do not limit the technical scope of the present invention.

Example 1

(1) Preparation of Photocurable Composition (a-1)

First, a component (A), a component (B), a component (C), and a surfactant component described below were blended to prepare a photocurable composition.

(1-1) component (A): a total of 100 parts by weight

<A-1> isobornyl acrylate (trade name: IB-XA produced by Kyoeisha Chemical Co., Ltd.): 61.6 parts by weight <A-2> (2-methyl-2-ethyl-1,3-dioxolan-4-yl)methyl acrylate (trade name: MEDOL-10 produced by Osaka Organic Chemical Industry Ltd.): 10 parts by weight <A-3> hexanediol diacrylate (trade name: Viscoat #230 produced by Osaka Organic Chemical Industry Ltd.): 22.4 parts by weight (1-2) component (B): a total of 3 parts by weight
<B-1> Irgacure 651 (produced by BASF): 3 parts by weight (1-3) component (C): hydrogen donor NIT-34 represented by formula (C-1) below: 0.5 parts by weight

[Chem. 13]

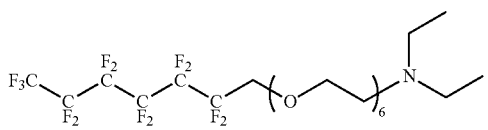

(C-1)

(1-4) surfactant component: pentadecaethylene glycol mono-1H,1H,2H,2H-perfluorooctyl ether ($F(CF_2)_6CH_2CH_2(OCH_2CH_2)_{15}OH$, produced by DIC Corporation): 1.1 parts by weight (2) Evaluation of Photopolymerization Rate by Attenuated Total Reflection Infrared Spectroscopy About 10 microliters of the photocurable composition (a-1) was sampled and dropped onto a diamond ATR crystal on an attenuated total reflection infrared spectrometer to form a coating film. Then a quartz glass having a thickness of 1 mm was placed on the coating film of the photocurable composition (a-1).

Light from an UV light source equipped with an ultra high pressure mercury lamp was applied to the coating film through an interference filter described below and the quartz glass for 10 seconds. The interference filter used in the irradiation was VPF25C-10-15-31300 (produced by Sigma Koki Co., Ltd.). The UV light used for irradiation was single wavelength ultraviolet light having a wavelength of 313 plus or minus 5 nm and the illuminance was 1 $mW/cm^2$. In the irradiation step, the rate of decrease in the number of acryl groups contained in the component (A) in the photocurable composition (polymerization reaction rate of the component (A)) was evaluated by the following method.

At the same time as starting the irradiation of the coating film, measurement of the attenuated total reflection infrared spectra was started, and data was acquired 2.7 times per second while continuing the irradiation. The minimum exposure (half decay exposure) required for the area intensity of the peak at 810 $cm^{-1}$ attributable to the acryl groups in the component (A) to become half the initial value observed immediately after start of the irradiation was 9.3 $mJ/cm^2$. This value was smaller than those of a photocurable composition (b-1) of Comparative Example 1 and a photocurable composition (b-2) of Comparative Example 2 described below. In other words, since the photocurable composition (a-1) is satisfactorily cured in a short exposure time compared to the photocurable compositions (b-1) and (b-2), a photo-nanoimprinting method that uses the photocurable composition (a-1) can be considered as highly productive.

(3) Measurement of Mold Releasing Force

Mold releasing force was measured by the method described below.

(3-1) Placement Step

Onto a 300 mm silicon wafer having an adhesion promoting layer 3 nm in thickness as an adhesive layer, a total of 1440 droplets (11 pL per droplet) of the photocurable composition (a-1) were dropped by an ink jet method. The droplets were dropped at pitches substantially equal to one another in a region having a length of 26 mm and a width of 33 mm.

(3-2) Mold Contact Step and Irradiation Step

A 28 nm line-and-space (L/S) pattern was formed in the photocurable resin composition (a-1) on the silicon wafer and a quartz mold (26 mm in length and 33 mm in width) not subjected to surface treatment was brought into contact with the photocurable composition (a-1).

Thirty seconds after the quarts mold was brought into contact with the photocurable composition (a-1), UV light was applied to the photocurable composition through the quartz mold by using an UV light source (EXECURE 3000 produced by HOYA CANDEO OPTRONICS CORPORATION) equipped with a 200 W mercury xenon lamp. In applying the UV light, an interference filter (VPF-50C-10-25-31300 produced by Sigma Koki Co., Ltd.) that selectively transmitted light with a wavelength of 313 plus or minus 5 nm was interposed between the UV light source and the quartz mold. The illuminance of the UV light directly below the quartz mold was 38.5 $mW/cm^2$ for light having a wavelength of 313 nm. The UV light was applied for 0.75 seconds under these conditions.

(3-3) Mold Releasing Step

Next, the quartz mold was pulled up at 0.5 mm/s to release the photocured film from the mold. The force required to release the cured film from the mold was measured by using a compact tension/compression load cell (LUR-A-200NSA1 produced by Kyowa Electronic Instruments Co., Ltd.). In actual measurement, the mold releasing force measurement was conducted three times under the same conditions and the average was calculated from the measurement data. As a result, the average mold releasing force was 59.0 N. This was lower than that of the photocured product prepared from the photocurable composition (b-1) in Comparative Example 1 described below.

Comparative Example 1

A photocurable composition (b-1) was prepared as in EXAMPLE 1 except that the component (C) (hydrogen donor) was not added.

The photopolymerization rate of the photocurable composition (b-1) was measured as in EXAMPLE 1. The half decay exposure was 13.8 $mJ/cm^2$.

The average mold releasing force for the photocured product obtained from the photocurable composition (b-1) was measured as in EXAMPLE 1. The average mold releasing force was 63.4 N.

Comparative Example 2

A photocurable composition (b-2) was prepared as in EXAMPLE 1 except that 0.5 parts by weight of a known hydrogen donor N-phenyl glycine was added instead of the component (C) (hydrogen donor).

The photopolymerization rate of the photocurable composition (b-2) was evaluated as in EXAMPLE 1. The half decay exposure was 11.7 $mJ/cm^2$.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-099551, filed May 9, 2013, which is hereby incorporated by reference herein in its entirety.

The invention claimed is:

1. A photocurable composition comprising:
   a component (A) which is a polymerizable compound;
   a component (B) which is a photopolymerization initiator; and
   a component (C) which is a compound represented by general formula (1):

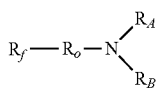

General formula (1)

where $R_f$ represents an alkyl group at least part of which is substituted with fluorine, $R_O$ represents a repeated structure of an oxyalkylene group or an oxypropylene group, N represents a nitrogen atom, $R_A$ represents an alkyl group, and $R_B$ represents an alkyl group or a hydrogen atom.

2. A photocurable composition comprising:
   a component (A) which is a polymerizable compound;
   a component (B) which is a photopolymerization initiator; and
   a component (C) which is a compound represented by general formula (1):

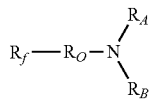

General formula (1)

where $R_f$ represents an alkyl group at least part of which is substituted with fluorine, $R_O$ represents an oxyalkylene group or a repeated structure of an oxyalkylene group, N represents a nitrogen atom, $R_A$ represents an alkyl group, and $R_B$ represents an alkyl group or a hydrogen atom.

3. The photocurable composition according to claim 2, wherein $R_B$ represents an alkyl group.

4. The photocurable composition according to claim 3, wherein $R_A$ and $R_B$ each represent a linear alkyl group having 1 to 5 carbon atoms.

5. The photocurable composition according to claim 2, wherein the compound represented by general formula (1) is a compound represented by general formula (5):

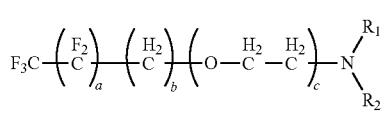

General formula (5)

where a represents an integer in a range of 1 to 25, b represents an integer in a range of 0 to 25, c represents an integer in a range of 1 to 25, $R_1$ represents an alkyl group, and $R_2$ represents an alkyl group or hydrogen.

6. The photocurable composition according to claim 5, wherein a, b, and c in general formula (5) each independently represent an integer in a range of 1 to 10.

7. The photocurable composition according to claim 5, wherein b in general formula (5) represents an integer in a range of 1 to 5.

8. The photocurable composition according to claim 5, wherein $R_2$ in general formula (5) represents an alkyl group.

9. The photocurable composition according to claim 8, wherein $R_1$ and $R_2$ in general formula (5) each represent a linear alkyl group having 1 to 5 carbon atoms.

10. A method for producing a patterned film, the method comprising:
    a placement step of placing the photocurable composition according to claim 2 on a substrate;
    a mold contact step of bringing the photocurable composition into contact with a mold having an original pattern for transferring a pattern shape;
    an irradiation step of irradiating the photocurable composition with light to form a cured film; and
    a mold releasing step of releasing the cured film from the mold.

11. The method according to claim 10, wherein a surface of the original pattern of the mold has hydroxyl groups.

12. The method according to claim 11, wherein the surface of the original pattern of the mold is composed of quartz.

13. The method according to claim 10, wherein the mold contact step is performed in an atmosphere composed of a gas containing a condensable gas.

14. The method according to claim 13, wherein the gas containing the condensable gas is a gas mixture containing helium and the condensable gas.

15. The method according to claim 13, wherein the condensable gas is 1,1,1,3,3-pentafluoropropane.

16. A method for producing an optical component, the method comprising:
    a step of obtaining a patterned film on a substrate by the method according to claim 10.

17. A method for producing an optical component, the method comprising:
    a step of obtaining a patterned film by the method according to claim 10; and
    a step of etching or ion-implanting the substrate by using a pattern shape of the obtained patterned film as a mask.

18. A method for producing a circuit board, the method comprising:
    a step of obtaining a patterned film by the method according claim 10;
    a step of etching or ion-implanting the substrate by using a pattern shape of the obtained patterned film as a mask; and
    a step of forming an electronic part on the substrate.

19. A method for forming an electronic component, the method comprising:
    a step of obtaining a circuit board by the method according to claim 18; and
    a step of connecting the circuit board to a controlling mechanism for controlling the circuit board.

20. A cured product obtained by curing the photocurable composition according to claim 2.

21. The photocurable composition according to claim 2, wherein a blend ratio of the component (C) is 0.001% by weight or more and 10% by weight or less relative to a total weight of the polymerizable compound serving as the component (A).

22. The photocurable composition according to claim 2, further comprising a hydrogen donor, wherein the ratio of the hydrogen donor is 0% or more and 20% by weight or less relative to a total weight of the polymerizable compound serving as the component (A).

23. The photocurable composition according to claim 2, wherein a viscosity of the photocurable composition is 5 cP or more and 50 cP or less in terms of a viscosity of a mixture of the components other than a solvent at 23° C.

* * * * *